(12) United States Patent
Izume

(10) Patent No.: US 10,507,672 B2
(45) Date of Patent: *Dec. 17, 2019

(54) CAN INSPECTION DEVICE

(71) Applicants: I. MER CO., LTD., Kyoto-shi (JP); NIPPON NATIONAL SEIKAN COMPANY, LTD., Ishioka-shi (JP)

(72) Inventor: Masayuki Izume, Kyoto (JP)

(73) Assignees: I. MER CO., LTD., Kyoto-Shi (JP); NIPPON NATIONAL SEIKAN COMPANY, LTD., Ishioka-Shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/820,442

(22) Filed: Nov. 22, 2017

(65) Prior Publication Data

US 2018/0093496 A1 Apr. 5, 2018

Related U.S. Application Data

(62) Division of application No. 15/024,034, filed as application No. PCT/JP2014/075021 on Sep. 22, 2014, now Pat. No. 9,862,204.

(30) Foreign Application Priority Data

Sep. 24, 2013 (JP) .................. 2013-196878
Sep. 24, 2013 (JP) .................. 2013-196880
Sep. 24, 2013 (JP) .................. 2013-196884

(51) Int. Cl.
*G01N 21/952* (2006.01)
*B41F 17/22* (2006.01)
(Continued)

(52) U.S. Cl.
CPC ............ *B41J 3/4073* (2013.01); *B41F 13/14* (2013.01); *B41F 17/22* (2013.01); *B41F 31/12* (2013.01);
(Continued)

(58) Field of Classification Search
CPC ...... B41F 31/02; B41F 31/14; B41F 33/0036; B41F 33/0045; B41F 33/14; B41F 17/08;
(Continued)

(56) References Cited

U.S. PATENT DOCUMENTS

| 6,519,356 | B1* | 2/2003 | Hooker | ............. G01N 21/9036 |
| | | | | 209/524 |
| 6,525,333 | B1 | 2/2003 | Hooker et al. | |
| 7,545,972 | B2* | 6/2009 | Itoh | ......................... G06K 9/00 |
| | | | | 382/142 |

FOREIGN PATENT DOCUMENTS

| EP | 1162064 | 12/2001 |
| JP | 58-49256 | 3/1983 |

(Continued)

OTHER PUBLICATIONS

International Search Report for corresponding International Application No. PCT/JP2014/075021, dated Jan. 6, 2015.
(Continued)

*Primary Examiner* — Leslie J Evanisko
(74) *Attorney, Agent, or Firm* — Mori & Ward, LLP

(57) ABSTRACT

A can inspection device includes a rotation device rotating cans, an imaging device taking images of rotating cans, and an image processor processing taken images. The imaging device includes a first camera taking an image of an entire can and a second camera taking an image of an opening-side end portion of the can. The image processor includes an image inspection means for inspecting whether printing is performed properly as compared with a master image by using the image taken by the first camera, a density measurement means for measuring densities in designated positions for respective colors by using the image taken by the first camera, and a printing misalignment value measurement means for measuring misalignment values with respect to set positions of printing misalignment inspection marks (Continued)

printed on the opening-side end portion of the can for respective colors by using the image taken by the second camera.

6 Claims, 15 Drawing Sheets

(51) Int. Cl.
| | |
|---|---|
| *B41J 3/407* | (2006.01) |
| *B41F 31/12* | (2006.01) |
| *B41F 31/14* | (2006.01) |
| *B41F 33/00* | (2006.01) |
| *B41F 13/14* | (2006.01) |
| *G01N 21/956* | (2006.01) |
| *G01N 21/90* | (2006.01) |

(52) U.S. Cl.
CPC .......... *B41F 31/14* (2013.01); *B41F 33/0045* (2013.01); *B41F 33/0081* (2013.01); *G01N 21/956* (2013.01); *B41P 2233/13* (2013.01); *B41P 2233/51* (2013.01); *B41P 2233/52* (2013.01); *G01N 21/909* (2013.01)

(58) Field of Classification Search
CPC .......... B41F 17/14; B41F 17/20; B41F 17/22; B41F 17/16; G01N 21/88; G01N 21/90; G01N 21/909; G01N 21/956; G01N 2021/845; G01N 2021/8455; G01N 21/952; G06T 7/0002; G06T 7/0004

USPC .................. 382/141, 142; 356/239.4, 239.8
See application file for complete search history.

(56) References Cited

FOREIGN PATENT DOCUMENTS

| | | | |
|---|---|---|---|
| JP | 5-126762 | 5/1993 | |
| JP | 06174649 A * | 6/1994 | |
| JP | 7-186374 | 7/1995 | |
| JP | 9-295396 | 11/1997 | |
| JP | 11-320838 | 11/1999 | |
| JP | 2001-129968 | 5/2001 | |
| JP | 2004-525340 | 8/2004 | |
| JP | 2004-251855 | 9/2004 | |
| JP | 2011-73415 | 4/2011 | |
| WO | WO-9641299 A1 * | 12/1996 | ......... G01N 21/9036 |
| WO | WO 2012/054655 | 4/2012 | |
| WO | WO 2016/087876 | 6/2016 | |

OTHER PUBLICATIONS

Extended European Search Report for corresponding EP Application No. 14848076.7-1704, dated Mar. 6, 2017.
Office Action with Form PTO-892 Notice of References Cited issued by the U.S. Patent and Trademark Office for U.S. Appl. No. 15/024,034, dated Jun. 8, 2017.

* cited by examiner

CAN INSPECTION DEVICE

CROSS-REFERENCE TO RELATED APPLICATIONS

The present application is a divisional application of the U.S. patent application Ser. No. 15/024,034 filed Mar. 23, 2016, which is a U.S. National Stage application of International Application No. PCT/JP2014/075021, filed Sep. 22, 2014, which claims priority under 35 U.S.C. § 119 to Japanese Patent Application No. 2013-196878, filed Sep. 24, 2013, Japanese Patent Application No. 2013-196880, filed Sep. 24, 2013, and Japanese Patent Application No. 2013-196884, filed Sep. 24, 2013. The contents of these applications are incorporated herein by reference in their entirety.

TECHNICAL FIELD

The present invention relates to a can inspection device.

BACKGROUND ART

As a printer for cans, there has been known one which includes a can supply means for supplying cans, plural ink supply means for supplying ink for respective colors, plural plate cylinders provided so as to correspond to respective ink supply means, to which ink supplied from the ink supply means is applied and a blanket transferring ink to cans supplied from the can supply means after the ink is sequentially transferred from respective plate cylinders (Patent Literature 1).

There is also disclosed in Patent Literature 2 an inspection device performing inspections of print states of cans which includes a rotation device rotating cans, an imaging device taking images of rotating cans and an image processor processing the taken images.

In Patent Literature 2, the image processor has an image inspection means for inspecting whether printing is performed properly as compared with a master image, in which a lack of printing, a stain in appearance and so on are inspected by the image inspection means.

CITATION LIST

Patent Literature

Patent Literature 1: JP-A-2001-129968
Patent Literature 2: JP-A-5-126762

SUMMARY OF INVENTION

Technical Problem

The above related-art printer for cans and the can inspection device are respectively used as independent devices, and inspection results obtained in the can inspection device are not reflected on the control of the printer.

In the inspections by the can inspection device, it is possible to perform an inspection for determining whether the product is good or bad in appearance, however, the density and printing misalignment have not been inspected, which are necessary for improving printing accuracy of the printer. Accordingly, concerning defects in density, an operator changes an ink supply amount in the printer after a defective product is found by a visual inspection, therefore, there is a problem that measures for defects in density are delayed and many defective products are manufactured.

Similarly, concerning defects in printing misalignment, an operator performs registration in the printer after a defective product is found by a visual inspection, therefore, there is a problem that measures for defects in printing misalignment are delayed and many defective products are manufactured.

An object of the present invention is to provide a can inspection device capable of measuring densities and printing misalignment values necessary for improving printing accuracy of a printer.

Solution to Problem

According to an embodiment of the present invention, there is provided a can inspection device including a rotation device rotating cans, an imaging device taking images of rotating cans, and an image processor processing taken images, which is provided in a can printing apparatus, performing inspections of print states of the cans and feeding back inspection results to the can printing apparatus, in which the imaging device includes a first camera taking an image of the entire can and a second camera taking an image of an opening-side end portion of the can, the image processor includes an image inspection means for inspecting whether printing is performed properly as compared with a master image by using the image taken by the first camera, a density measurement means for measuring densities in designated positions for respective colors by using the image taken by the first camera, and a printing misalignment value measurement means for measuring misalignment values with respect to set positions of printing misalignment inspection marks printed on the opening-side end portion of the can for respective colors by using the image taken by the second camera.

The first camera is one which has been used from the past for inspecting images, and image inspection and density measurement can be performed by using the first camera. The second camera takes only images of opening-side end portions of cans.

In the inspection by the image inspection means, the master image and the taken image are compared pixel by pixel, and a partial lack, a stain due to ink scattering and so on in the image are inspected.

In the inspection by the density measurement means, densities in designated places (density measurement places) for respective colors are measured. The density measurement results are fed back to the printer, thereby correcting densities before a defective product in density is found. Accordingly, better print states can be maintained.

The printing misalignment inspection marks are printed on the opening-side end portion of the can for respective colors, an image of which is taken by the second camera, and printing misalignment values are calculated by the printing misalignment value measurement means. The printing misalignment value measurement results are fed back to the printer, thereby correcting (registration) the printing misalignment values (positional deviations of plate cylinders of the printer) before a defective product in printing misalignment is found and maintaining better print states.

It is preferable that the rotation device includes a vertical drive side rotating shaft driven by a motor, a vertical driven side rotating shaft rotating integrally with the drive side rotating shaft, a cylindrical holding member attached concentrically to the driven side rotating shaft so as to hold a can and an encoder detecting a rotation of the drive side rotating shaft, and the drive side rotating shaft and the driven side rotating shaft face each other in the axial direction in a state of being positioned in a vertical direction, and magnets applying attracting forces to each other are provided to a lower end portion of the drive side rotating shaft and an upper end portion of the driven side rotating shaft, thereby allowing the drive side rotating shaft and the driven side rotating shaft to rotate integrally.

When taking images, the rotation device which can accurately turn the can once is necessary. In the rotation device, the drive side rotation shaft and the driven side rotation shaft are integrally rotated by attracting forces of the magnets, thereby turning the can once accurately. Though a slight gap may exist between the drive side rotation shaft and the driven side rotation shaft, it is preferable no gap exists for increasing the attracting forces.

Advantageous Effects of Invention

When adopting the can inspection device according to the present invention, densities and printing misalignment values which have not been able to be measured can be measured. Therefore, printing accuracy can be improved by reflecting the measurement results on printing conditions of the printer.

Figure 1:
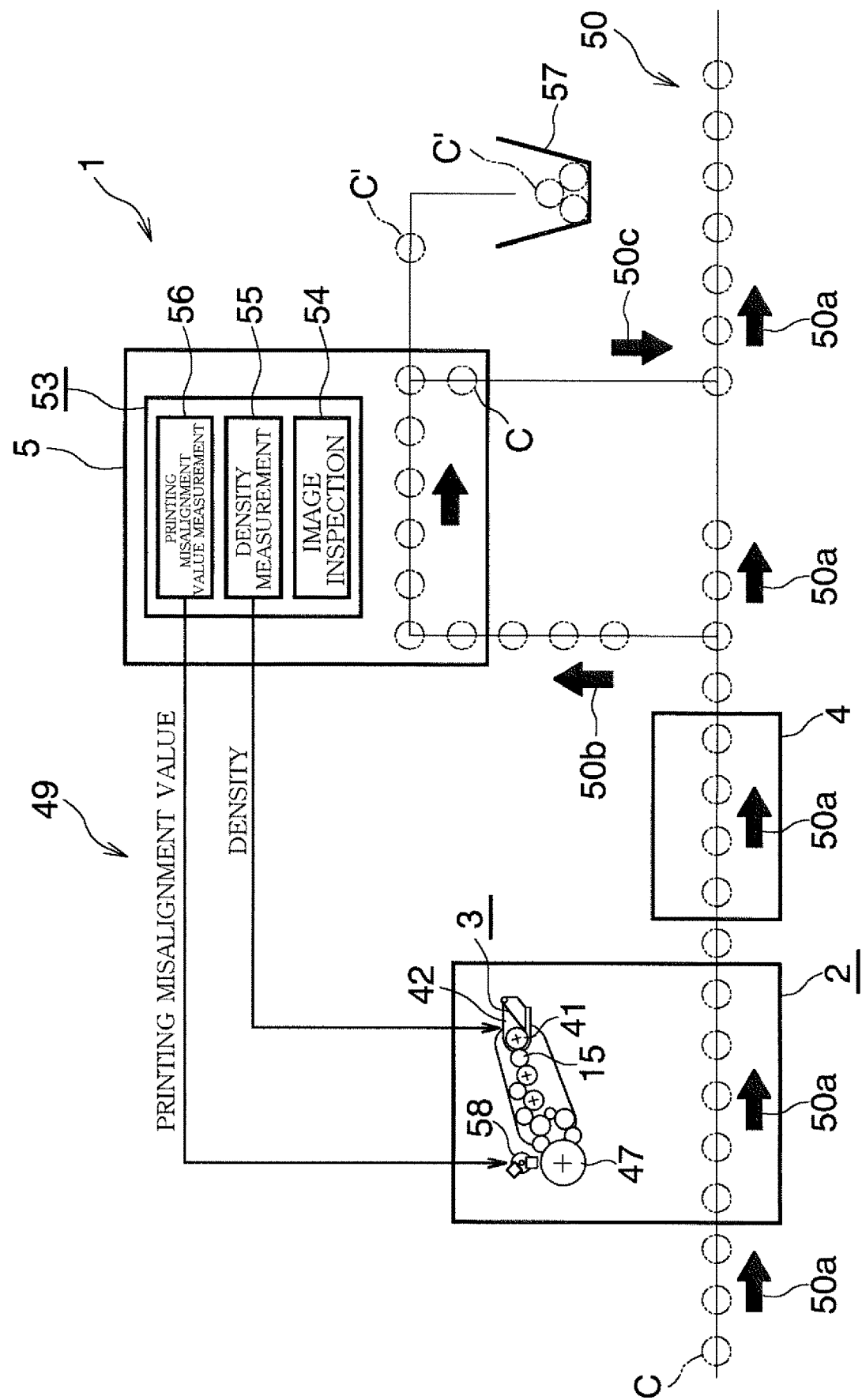
FIG. 1 is a block diagram showing a can printing apparatus according to an embodiment of the present invention.

REFERENCE SIGNS LIST (1) can printing apparatus
(2) printer
(3) ink supply device
(5) can inspection device
(47) plate cylinder
(47a) plate cylinder shaft
(51) rotation device
(52) imaging device
(53) image processor
(54) image inspection means
(55) density measurement means
(56) printing misalignment value measurement means
(74) driven side rotating shaft
(75) holding member
(77) drive side rotating shaft
(78) motor
(77) (78) magnets
(79) first camera
(80) second camera
(96) axial direction moving means
(97) circumferential direction moving means
(98) axial direction drive means
(99) circumferential direction drive means
(101) housing
(102) sleeve (axial direction moving means)
(104) spline cylinder (circumferential direction moving member
(106) helical gear
(109) first motor
(110) second motor
(111) outer side rotation shaft (first rotation shaft)
(111a) male screw portion
(112) inner side rotation shaft (second rotation shaft)
(112a) male screw portion
(119) first female screw member
(120) second female screw member
(124) first motor controller
(125) second motor controller

DESCRIPTION OF EMBODIMENTS

Hereinafter, embodiments of the present invention will be explained with reference to the drawings.

FIG. 1 shows a can printing apparatus (1) according to an embodiment of the present invention. The can printing apparatus (1) includes a printer (2) performing printing to cans (C), a drier (4) drying printing surfaces of the cans (C) after the printing, a can inspection device (5) inspecting print states of printing surfaces, an inspection result feedback controller (49) feeding back inspection results of the can inspection device (5) to the printer (2) and changing printing conditions of the printer (2) based on inspection results of the can inspection device (5) and a conveyance device (50) conveying the cans (C).

The printer (2) performs printing to a cylindrical can body which opens at the top (a body of a two-body can, which will be referred to merely as a can (C)).

The cans (C) are transferred to a downstream side through the drier (4) after being printed in the printer (2). Print states of part of a large number of cans (C) passing through the drier (4) are inspected in the can inspection device (5).

The conveyance device (50) includes a main line (50a) supplying the cans (C) to the printer (2) and transferring the printed cans (C) to the downstream side, a sampling line (50b) transferring part of a number of cans (C) passing through the driver (4) to the can inspection device (5) and a return line (50c) returning the cans (C) determined as good products in the can inspection device (5) to the main line (50a).

Figure 2:
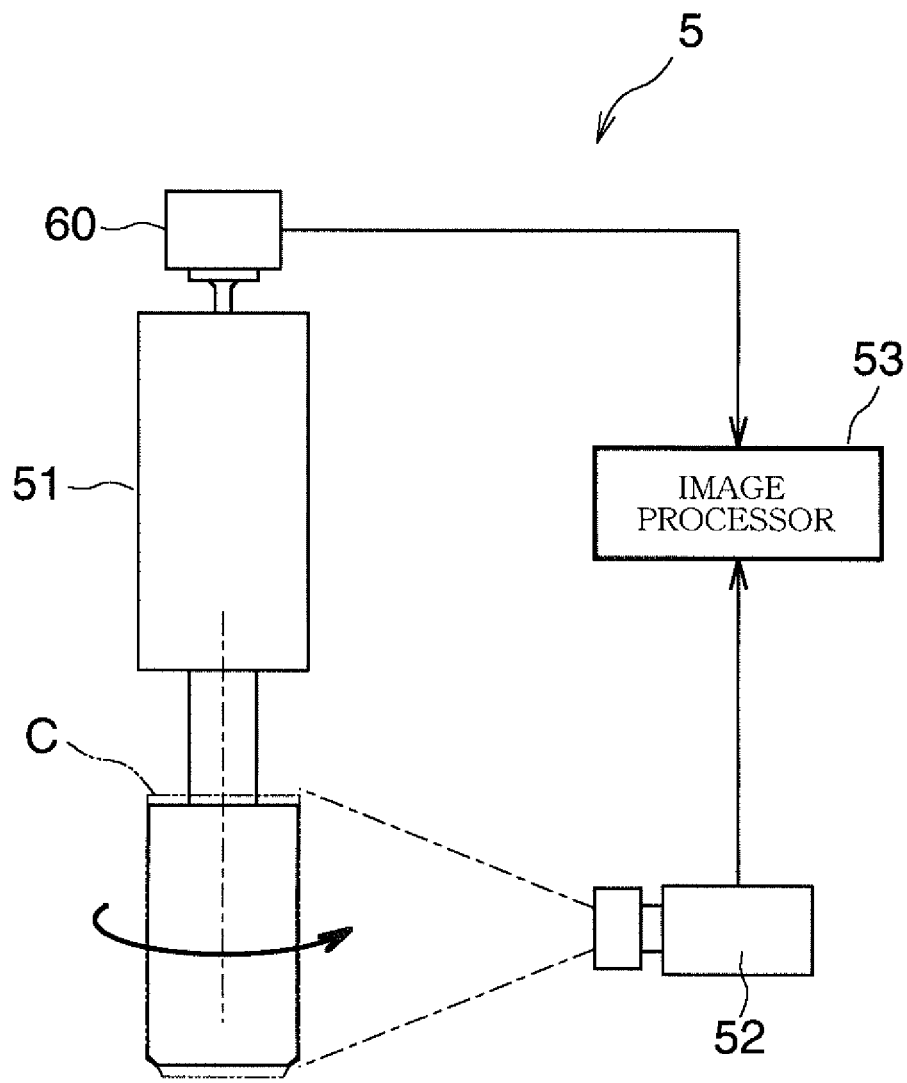
FIG. 2 is a view schematically showing an outline structure of a can inspection device.

In the can inspection device (5), as schematically shown in FIG. 2, the can (C) is rotated by a rotation device (51), a drive side of the rotation device (51) and the can (C) on the driven side are synchronized through an encoder (92), and an image is taken by an imaging device (52), then, the image is processed in an image processor (53).

The can inspection device (5) is provided with an image inspection means (54), a density measurement means (55) and a printing misalignment value measurement means (56) as the image processor (53) which processes the taken images as shown in FIG. 1. Cans (C) determined as good products in the can inspection device (5) are returned to the main line (50a) as described above, and cans (C') determined as inspection rejected products in the can inspection device (5) are discharged to an inspection rejected product storage part (57).

The density obtained in the density measurement means (55) and the printing misalignment value obtained in the printing misalignment value measurement means (56) in the can inspection device (5) are fed back to the printer (2) by the inspection result feedback controller (49). In the printer (2), the ink supply amount is adjusted by a controller (34) according to the density and a plate cylinder position is adjusted by an automatic registration device (58) according to the printing misalignment value.

Figure 3:
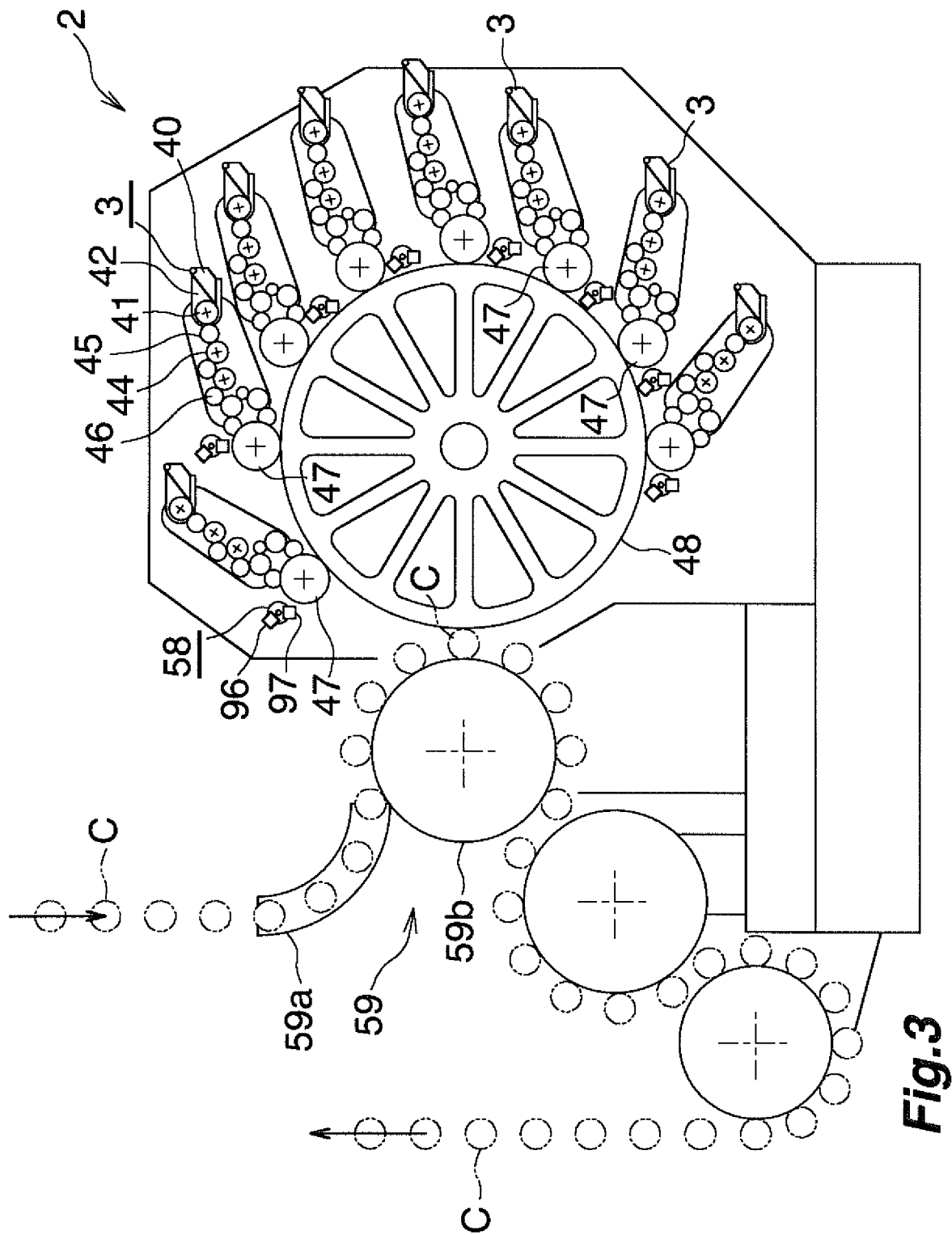
FIG. 3 is a side view showing a printer.
Figure 4:
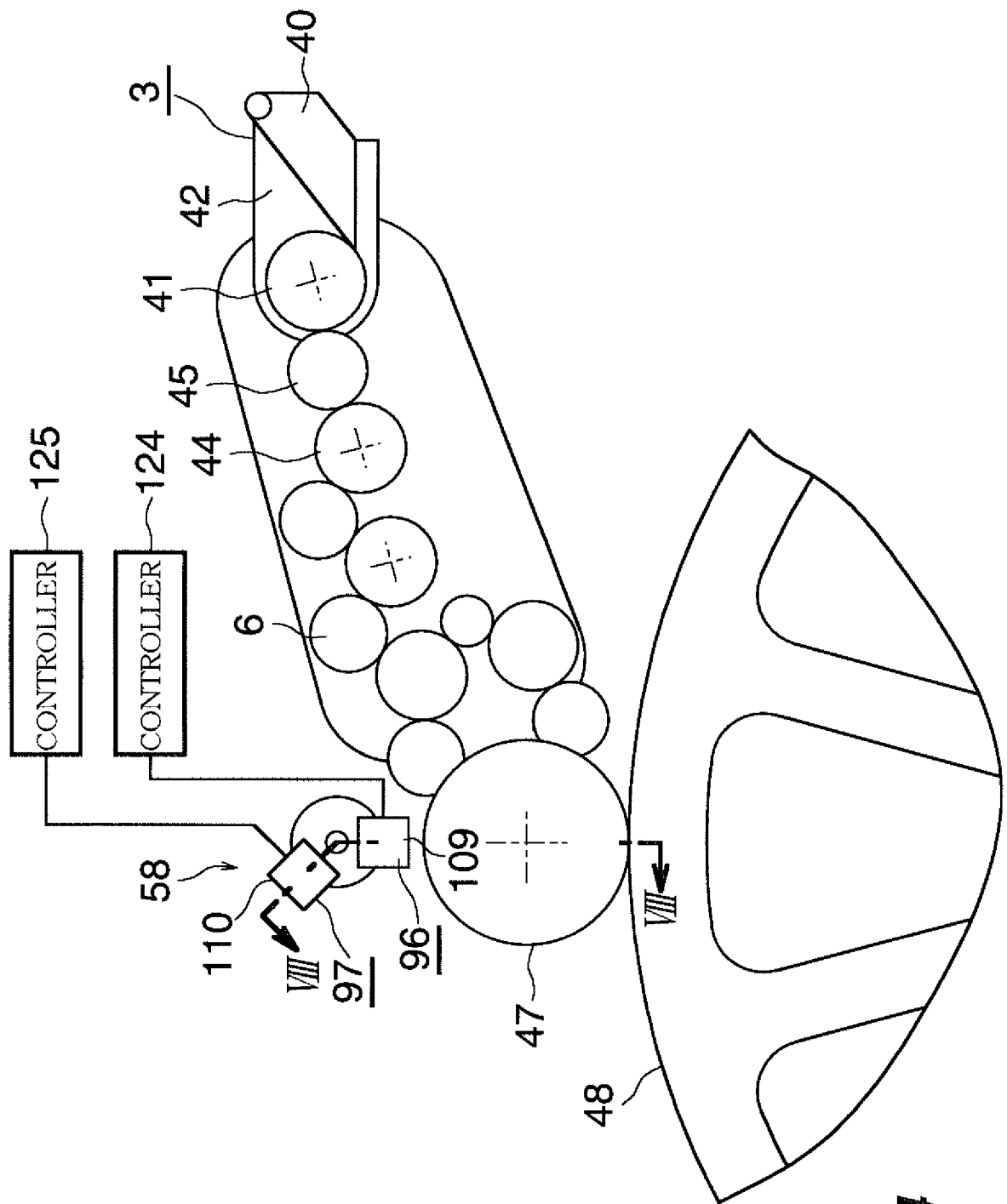
FIG. 4 is an enlarged side view of a main part of the printer.

The printer (2) includes plural (eight in the drawing) plate cylinders (47) having plates for printing different colors respectively, a blanket cylinder (48) performing printing to cans by the ink being transferred from the plate cylinders (47), ink supply devices (3) for supplying ink to respective plate cylinders (47), the registration devices (58) performing positional adjustment (registration) of the plate cylinders (47) and a can feeding device (59) having plural can feeding rollers (59b) and can feeding chutes (59a) as shown in FIG. 3 and FIG. 4.

The registration device (58) includes an axial direction moving means (96) for moving the plate cylinder (47) in the axial direction and a circumferential direction moving means (97) for moving the plate cylinder (47) in the circumferential direction. The registration device (58) is provided with controllers (124) (125) controlling motors (109) (110) provided in respective moving means (96) (97) as shown in FIG. 4.

Figure 5:
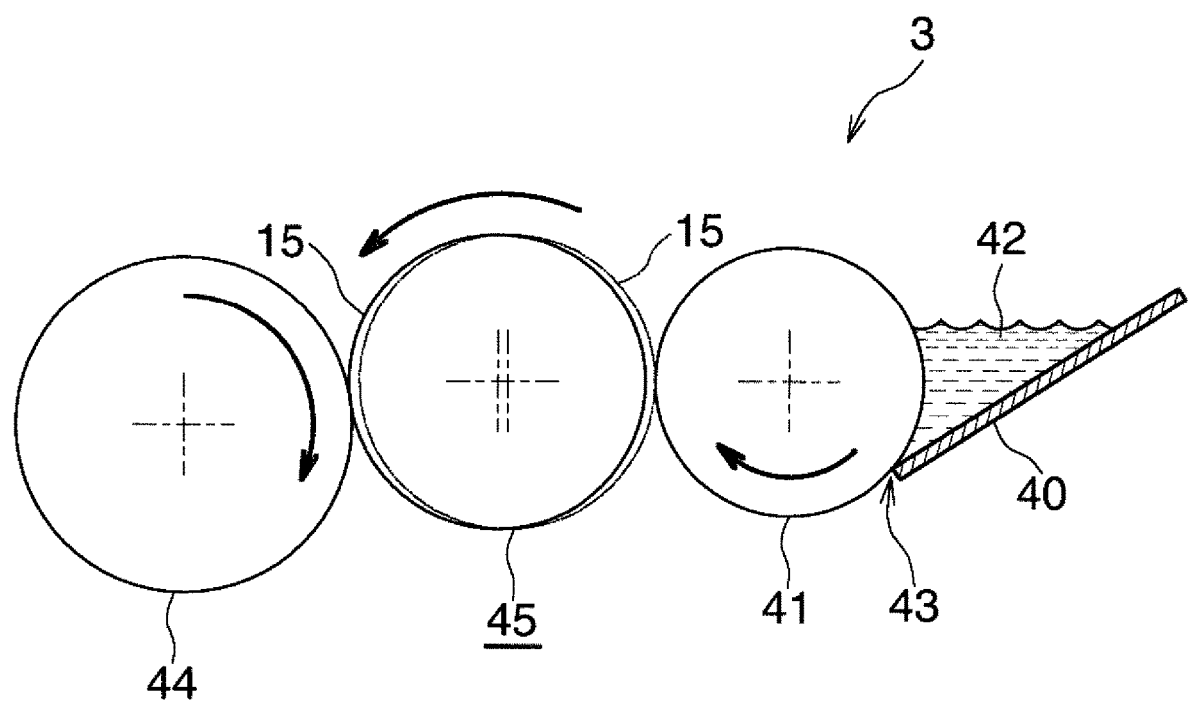
FIG. 5 is a schematic side view of a main part of an ink supply device of the printer.
Figure 6:
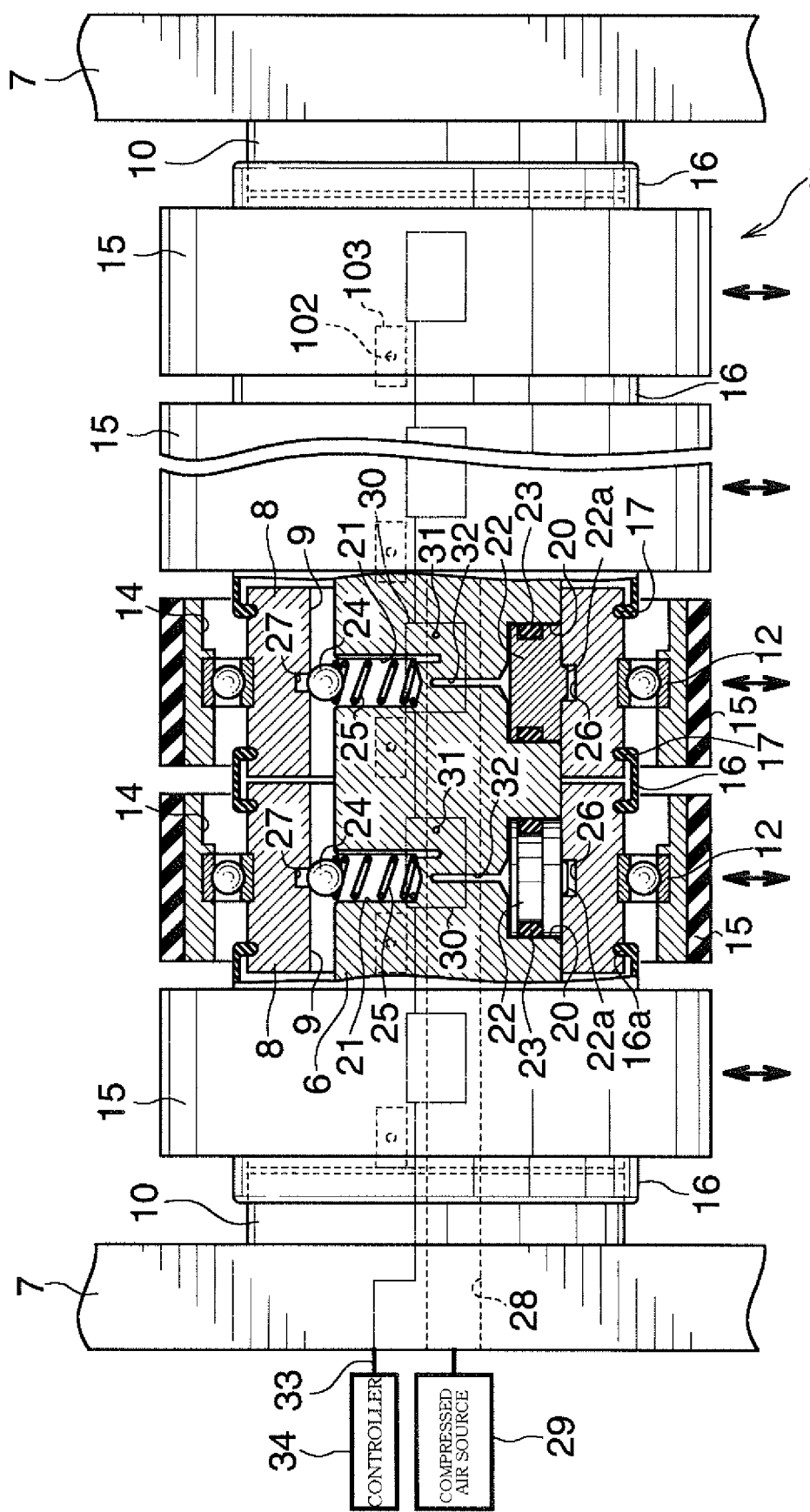
FIG. 6 is a partially cutaway plan view of an ink transfer roller unit of FIG. 5.
Figure 7:
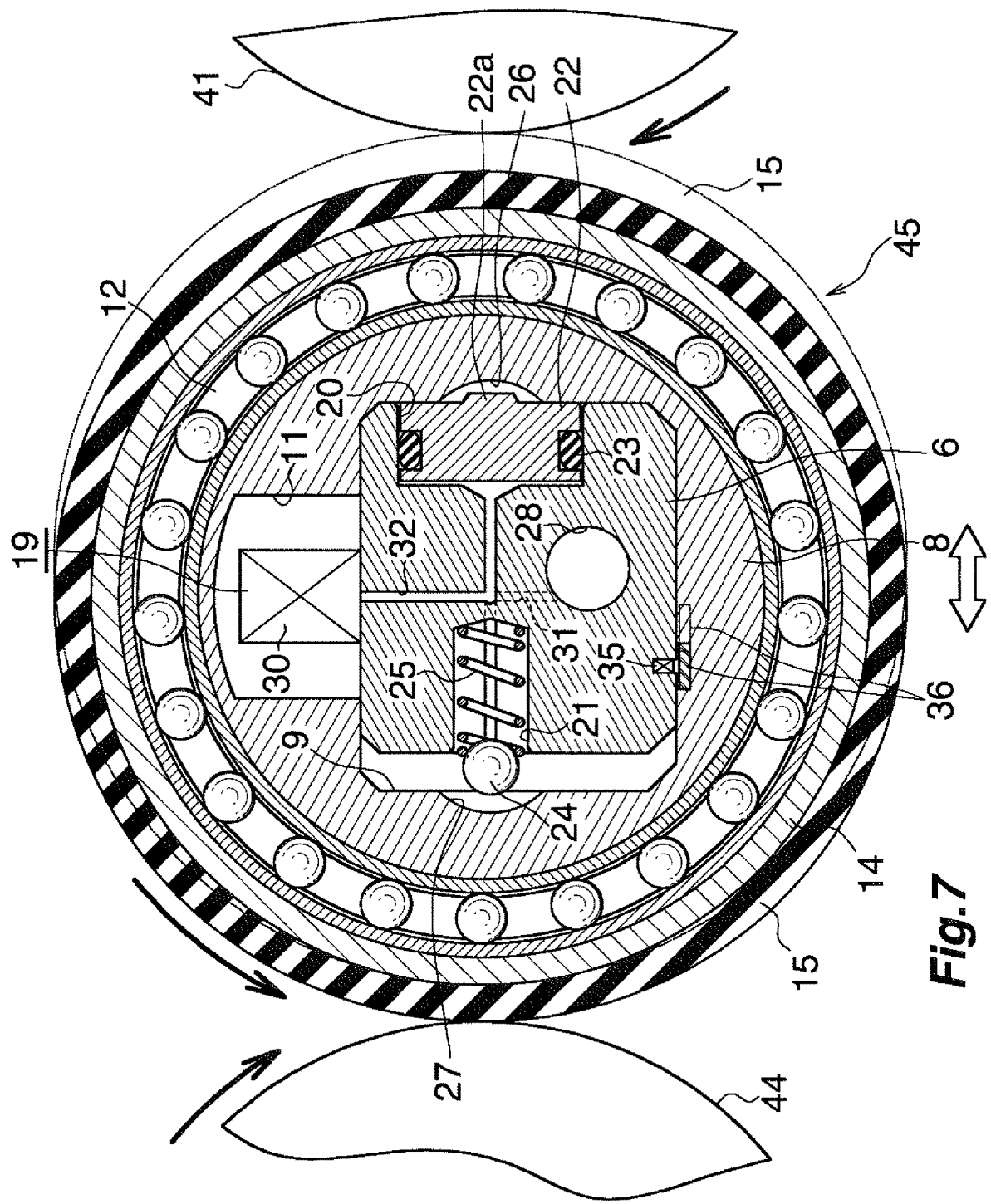
FIG. 7 is a horizontal cross-sectional view of FIG. 6.

FIG. 5 to FIG. 7 show the ink supply device. In the following explanation, the right side of FIG. 5 (the lower side of FIG. 6) corresponds to the front, the left side of FIG. 5 (the upper side of FIG. 6) correspond to the back, and left and right seen from the front correspond to left and right.

As shown in FIG. 5 in an enlarged manner, an inkwell roller (41) is arranged in the ink supply device (3) so as to be close to a rear end part of an inkwell member (40), which forms an inkwell (42), and an ink passage (43) having a given gap between the rear end part of the inkwell member (40) and the surface of the inkwell roller (41) is formed.

A first ink distributing roller (44) in plural ink distributing rollers (44) (46) is arranged in the rear direction of the inkwell roller (41), an ink transfer roller unit (45) is arranged between the inkwell roller (41) and the ink distributing roller (44) so as to be close to both rollers. The roller unit (45) is an aggregation of plural (seven in the drawing) ink transfer rollers (15) divided in the axial direction of the rollers (41) (44), and these ink transfer rollers (15) are arranged at small intervals in the axial direction. Shafts of these rollers (15) (41) (44) are parallel to one another and extend in a right and left direction. The inkwell roller (41) and the ink distributing roller (44) are rotatably supported by a frame (7) of the printer, and continuously rotated in an arrow direction of FIG. 4 at a rotation speed synchronized with each other by a not-shown drive device. For example, the rotation speed of the inkwell roller (41) is approximately 1/10 of that of the ink distributing roller (44).

The details of the ink transfer roller unit (45) are shown in FIG. 6 and FIG. 7. FIG. 6 is a partially cut-out plan view of the roller unit (45), and FIG. 7 is an enlarged horizontal cross-sectional view of FIG. 6 seen from the left side.

Right and left both ends of a straight support member (6) which is parallel to the rollers (41) (44) are fixed by the frame (7), and plural movable members (8) are attached around the support member (6). The support member (6) has a prismatic shape a front and rear width of which is slightly larger than a vertical width. The movable members (8) have a short columnar shape, and relatively large prismatic holes (9) penetrating the movable members (8) in the axial direction are formed in the movable members (8). The plural movable members (8) are aligned in the axial direction between a pair of short-columnar shaped fixing members (10) fixed to the frame (7) so as to face each other and penetrated by the support member (6), and the support member (6) penetrates through the holes (9) of these movable members (8). A vertical width of the holes (9) of the movable members (8) is approximately equal to the vertical width of the support member (6), and both vertical surfaces of the holes (9) slidingly contact both vertical surfaces of the support member (6). A front and rear width of the hole (9) is slightly larger than the front and rear width of the support member (6), and the movable members (8) are configured to move in the front and rear direction with respect to the support member (6) between a front end position where rear surfaces of the holes (9) contact a rear surface of the support member (6) and a rear end position where front surfaces of the holes (9) contact a front surface of the support member (6). A rectangular groove (11) is formed over the entire length of the movable member (8) on an upper surface of the hole (9) of the movable member (8) slidingly contacting the support member (6).

Respective movable members (8) are positioned in the axial direction with respect to the support member (6) as described later. Small gaps are provided in the axial direction between the movable members (8) mutually and between the movable members (8) and the fixing members (10) of both ends. Accordingly, respective movable members (8) can be individually moved in the front and rear direction with respect to the support member (6).

An inner ring of a ball bearing (12) as a rolling bearing is fixed to an outer periphery of each movable member (8). A metal sleeve (14) is fixed to an outer periphery of an outer ring of each ball bearing (12), and the thick cylindrical ink transfer roller (15) made of rubber is fixed to an outer periphery of the sleeve (14).

Short columnar dust proof members (16) are fitted between mutual outer peripheries of adjacent movable members (6). The dust proof member (16) is formed of appropriate rubber-state elastic materials such as natural rubber, synthetic rubber and synthetic resin, and flange portions (16a) slightly protruding to the inside are integrally formed at both ends thereof. These flange portions (16a) are fitted to annular grooves (17) formed on outer peripheral surfaces in portions close to right and left both ends of the movable member (8), thereby fixing the dust proofing member (16) to the movable member (8). Similar dust-proof members (16) are fitted between mutual outer peripheries of the movable members (8) on right and left both ends and the fixing members (10) adjacent to the members.

A roller position switching device (19) switching the position of the ink transfer roller (15) as described below is provided on the support member (6) side between each movable member (8) and the support member (6).

A hole slightly extending in the rear direction from the front surface is formed in a portion of the support member (6) corresponding to the central portion of the movable member (8) in the axial direction to thereby form a cylinder portion (20) and to form a spring housing hole (21) slightly extending to the front direction from the rear surface. The center of the cylinder portion (20) and the center of the spring housing hole (21) are on one straight line in the front and rear direction in the vicinity of the center of the movable member (8) in the vertical direction. A short columnar piston (22) is inserted into the cylinder portion (20) so as to be slidable in the front and rear direction through an O-ring (23). A ball (24) as a biasing member is inserted into the spring housing hole (21) so as to be slidable in the front and rear direction, and a compressed coil spring (25) biasing the ball (24) backward is inserted into the spring housing hole (21).

Concave portions (26) (27) are formed on the front surface of the hole (9) of the movable member (8) facing the center of the piston (22) and the rear surface of the hole (9) facing the center of the ball (24). The width of respective concave portions (26) (27) of the movable member (8) in the axial direction is fixed. Cross-sectional shapes of respective concave portions (26) (27) in a cross section orthogonal to the axis line of the movable member (8) are the same, which forms an arc shape around a straight line parallel to the axis line. A tapered projection (22a) is formed in the center of an end surface of the piston (22) facing the concave portion (26), and the projection (22a) is fitted to the concave portion (26). A length of the piston (22) excluding the projection (22a) is slightly shorter than a length of the cylinder portion (20), and most part of the projection (22a) projects from the front surface of the support member (6) even in a state where the piston (22) retreats into the cylinder portion (20) to the maximum. On the other hand, part of an outer periphery of the ball (24) is fitted to the concave portion (27).

In a rear part of the support member (6), the ball (24) is pressure contacted to the rear surface of the hole (9) of the movable member (8) constantly by an elastic force of a spring (25), and part of the outer periphery of the ball (24) is fitted to the concave portion (27) to be pressure contacted to an edge of the concave portion (27) in the front and rear direction. On the other hand, in a front part of the support member (6), the front surface of the support member (6) or the piston (22) is pressure contacted to the front surface of the hole (9) of the movable member (8), and most part of the projection (22a) of the piston (22) is fitted to the concave portion (26). Most part of the projection (22a) of the piston (22) and part of the ball (24) are fitted to the concave portions (26) (27) constantly as described above, thereby positioning the movable member (8) in the axial direction with respect to the support member (6).

An air supply hole (28) having a circular shape in cross section, which extends from the left end of the support member (6) in the axial direction to be closed in the vicinity of the right end is formed in the support member (6). A left-end opening end of the hole (28) is connected to a compressed air source (29) through a proper pipe.

A switching valve (solenoid valve) (30) is attached to an upper surface of the support member (6) facing the groove (11) of the movable member (8), and two ports of the valve (30) are respectively communicated to the air supply hole (28) and the cylinder portion (20) through communication holes (31) (32) formed in the support member (6). An electric wire (33) of the valve (30) is pulled out to the outside through a portion of the groove (11) and is connected to the controller (34).

The cylinder portion (20) is communicated to the air supply hole (28) through the valve (30) in a state where electric current is applied (on-state) to the valve (20) and the cylinder portion (20) is communicated to the air through the valve (30) in a state where electric current is stopped (off-state). The energized state of the valve (30) of each switching device (19) is individually switched by the controller (34), thereby individually switching the position of each ink transfer roller (15) in the front and rear direction.

When the valve (30) is switched to the off-state, the cylinder portion (20) is communicated to the air, therefore, the piston (22) is capable of moving in the cylinder portion (20) freely. Accordingly, the movable member (8) is moved to the rear side by the spring (25) through the ball (24). As a result, the movable member (8) and the ink transfer roller (15) are switched to the rear end position (non-transfer position), and the ink transfer roller (15) is separated from the inkwell roller (41) and pressure contacts the ink distributing roller (44).

When the valve (30) is switched to the on-state, the cylinder portion (20) is communicated to the air supply hole (28) and communicated to the compressed air source (29) through the air supply hole (28), therefore, compressed air is supplied to the cylinder portion (20). Accordingly, the piston (22) protrudes to the front direction from the support member (6) against the force of the spring (25), and the movable member (8) is moved forward accordingly. As a result, the movable member (8) and the ink transfer roller (15) are switched to the front end position (transfer position) and the ink transfer roller (15) is separated from the ink distributing roller (44) and pressure contacts to the inkwell roller (41).

A position switching detection sensor (35) including magnetic sensor is fixed in an embedded manner in a lower surface of the support member (6) slidingly contacting a bottom wall of the hole (9) of the movable member (8), and a permanent magnet (36) is fixed in an embedded manner in a bottom wall of the hole (9) of the movable member (8), which faces the sensor. A lower surface of the sensor (35) is flush with the lower surface of the support member (6) or positioned slightly inside (upper side) thereof. An upper surface of the permanent magnet (36) is flush with the bottom wall surface of the hole (9) of the movable member (8) or positioned slightly inside (lower side) thereof. In the state where the movable member (8) is switched to the rear end position, the sensor (35) faces the central part of the permanent magnet (36) in the front and rear direction. In the state where the movable member (8) is switched to the front end position, the sensor (35) is deviated rearward from the permanent magnet (36). Therefore, the output of the sensor (35) is changed according to the position of the movable member (8) and where the movable member (8) is, namely, the ink transfer roller (15) is recognized according to the output of the sensor (35).

The ink in the inkwell (42) comes out to the surface of the outer periphery of the inkwell roller (41) through the ink passage (43). A film thickness of the ink coming out to the surface of the inkwell roller (41) corresponds to the size of the gap of the ink passage (43), and the size of the gap of the ink passage (43) is adjusted, thereby adjusting the film thickness of the ink coming out to the surface of the inkwell roller (41). Normally, the size of the gap of the ink passage (43) is adjusted so that the film thicknesses of the ink are equivalent in all the ink transfer rollers (15). The ink coming out to the surface of the outer periphery of the inkwell roller (41) is transferred to the ink transfer roller (15) while the ink transfer rollers (15) are switched to the front end position. The ink transferred to respective ink transfer rollers (15) is transferred to the ink distributing roller (44) while the ink transfer rollers (15) are switched to the rear end position. The ink transferred to the ink distributing roller (44) is supplied to a print surface further through other plural ink distributing rollers which are not shown. Whether the switching of the position of the ink transfer rollers (15) is normal or not is detected by the output of the sensor (35), and an alarm is given when the ink transfer rollers (15) are not normally switched.

In the printer (2), the ink is transferred by switching the position of a required ink transfer roller (15) at transfer timings of given intervals, and a rotation angle (contact rotation angle) of the inkwell roller (41) made from a contact to the inkwell roller (41) until a separation form the inkwell roller (41) is controlled in each ink transfer roller (15) by the controller (34), thereby controlling a peripheral length of the ink transferred from the inkwell roller (41) to the ink transfer roller (15), as a result, the amount of ink supplied to the print surface is adjusted according to the position in the width direction.

The control of the contact rotation angle is performed by controlling a period of time (contact instruction period) from contact instruction (the output of a switching instruction to the transfer position with respect to the ink transfer roller (15)) until non-contact instruction (the output of a switching instruction to the non-transfer position.

In the case where the density of a certain color in eight colors is low, the contact period of the color in the ink supply device (3) is elongated, and in the case where the density of a certain color is high, the contact period of the color in the ink supply device (3) is shortened, thereby controlling the density.

Figure 8:
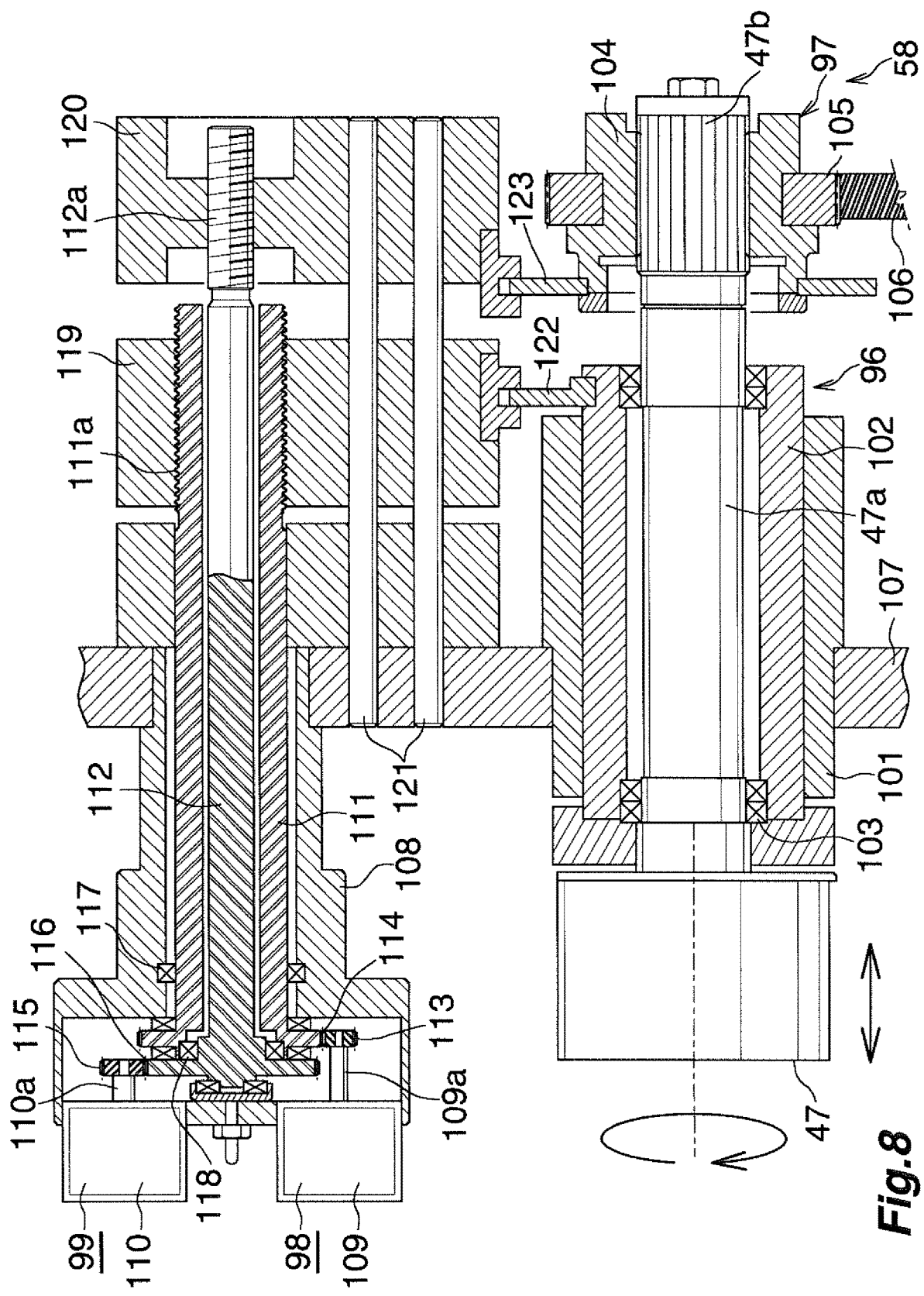
FIG. 8 is a vertical cross-sectional view of a registration device of the printer, which is the cross-sectional view taken along VIII-VIII line of FIG. 4.
Figure 9:
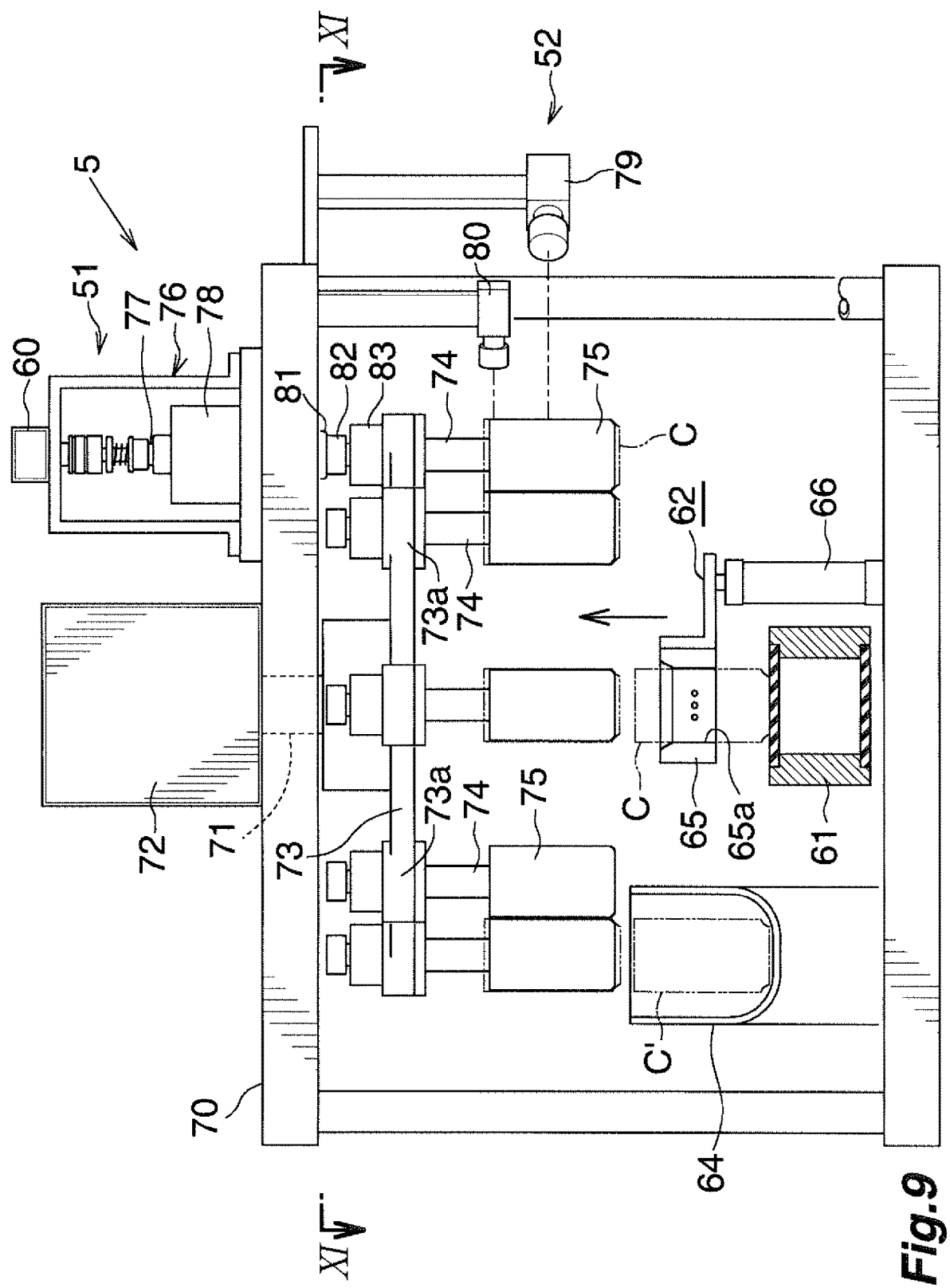
FIG. 9 is a front view of the can inspection device.
Figure 10:
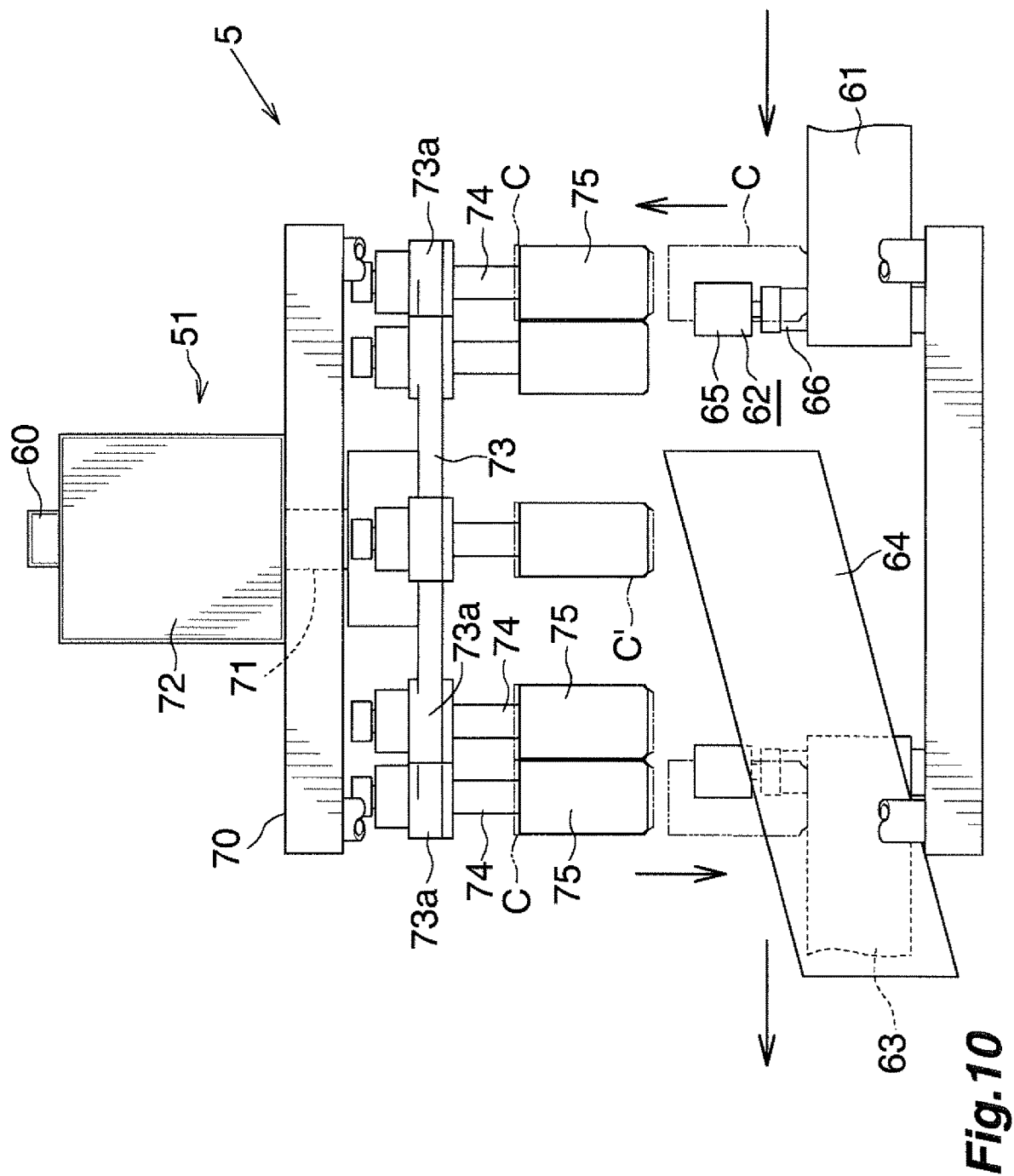
FIG. 10 is side view of FIG. 9.
Figure 11:
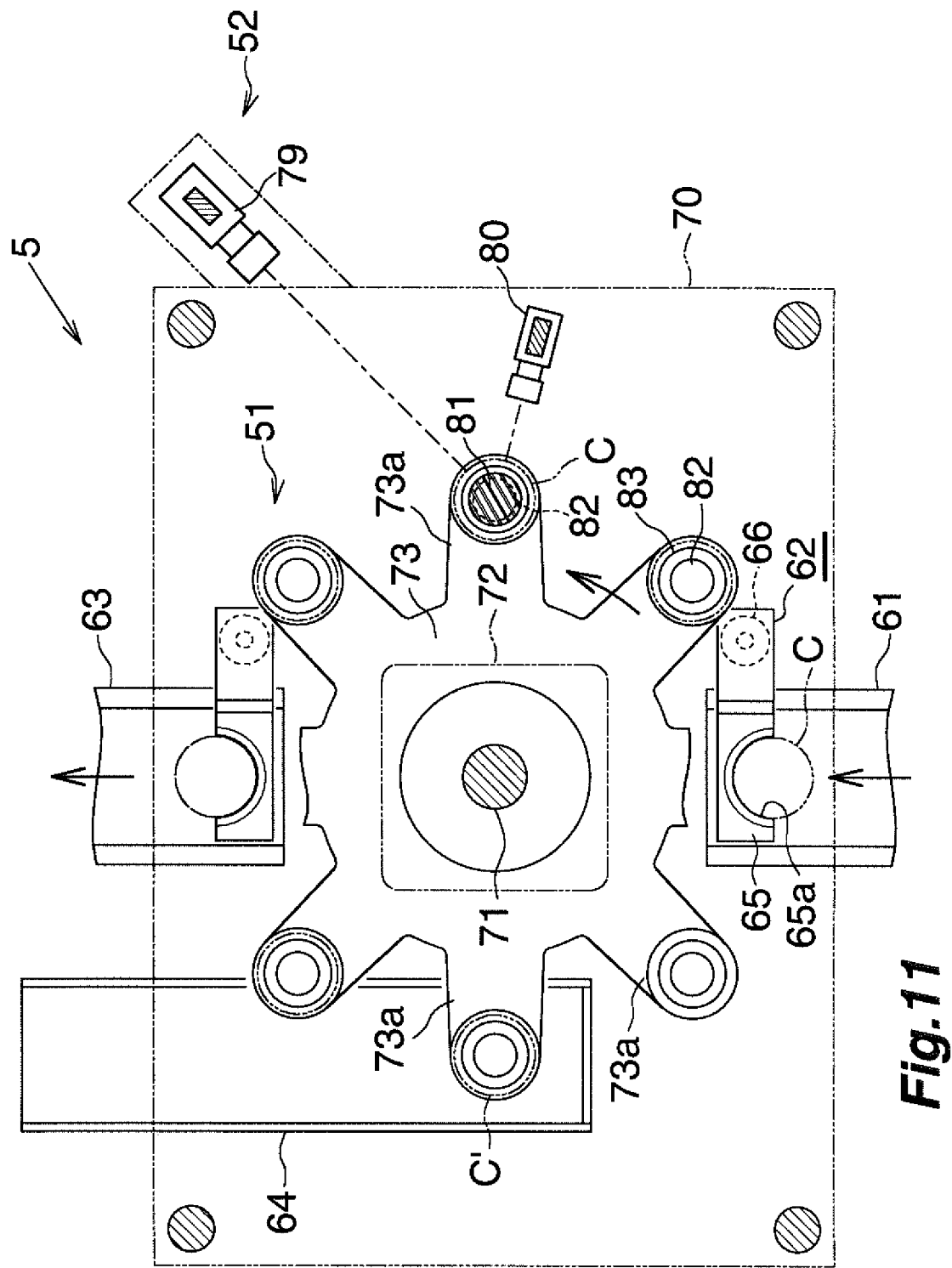
FIG. 11 is a cross-sectional view taken along XI-XI line of FIG. 9.

FIG. 8 shows the registration device (58) of the printer (2). In the explanation of the registration device (58), top/bottom and right/left correspond to top/bottom and right/left in FIG. 8.

As shown in FIG. 8, the axial direction moving means (96) moving the plate cylinder (47) in the right and left direction (axial direction) includes a sleeve (a cylindrical axial direction moving member) (102) moving in the axial direction integrally with a plate cylinder shaft (47a). The sleeve (102) is supported by a cylindrical plate cylinder shaft housing (101) so as not to rotate and so as to move in the axial direction. The plate cylinder shaft (47a) is supported by the sleeve (102) through a bearing (103) so as to rotate freely and so as not to move in the axial direction. The plate cylinder shaft (47a), the sleeve (102) and the plate cylinder shaft housing (101) are concentrically arranged.

The circumferential direction moving means (97) which moves the plate cylinder (47) to the circumferential direction includes a spline cylinder (circumferential direction moving member) (104) fitted to a spline shaft portion (47b) provided in a right end portion of the plate cylinder shaft (47a) extending in the right direction from the central portion of the plate cylinder (47). An annular groove is formed in an outer periphery of the spline cylinder (104), and a helical gear (105) is fitted into the annular groove and fixed therein. The helical gear (105) is engaged with a helical gear (106) arranged so as not to move in the axial direction. The spline cylinder (104) is attached to the spline shaft portion (47b), namely, the plate cylinder shaft (47a) by spline fitting so as to integrally move as well as so as to relatively move in the axial direction. The plate cylinder shaft (47a) moves in a circumferential direction with the movement of the spline cylinder (104) in the axial direction due to the engagement of the helical gears (105) (106) with each other.

The plate cylinder shaft housing (101) is fixed to a frame (107) orthogonal to the plate cylinder shaft housing (101). A right end portion of a motor housing (108) arranged in parallel to the plate cylinder shaft housing (101) above the plate cylinder shaft housing (101) is fixed to the frame (107).

In a left end of the motor housing (108), two motors, namely, a first motor (109) on a lower side (side close to the plate cylinder (47)) and a second motor (110) on an upper side (side apart from the plate cylinder (47)) are arranged.

In the motor housing (108), a hollow outer side rotation shaft (first rotation shaft) (111) rotated by the first motor (109) and a solid inner side rotation shaft (second rotation shaft) (112) arranged concentrically with the outer side rotation shaft (111) and rotated by the second motor (110) are arranged so as to rotate.

A drive gear (113) is attached to a right end portion of a drive shaft (109a) extending in the right direction of the first motor (109), and the drive gear (113) is engaged with a driven gear (114) provided integrally with a left end portion of the outer side rotation shaft (111). A drive gear (115) is attached to a right end portion of a drive shaft (110a) extending in the right direction of the second motor (110), and the drive gear (115) is engaged with a driven gear (116) provided integrally with a left end portion of the inner side rotation shaft (112).

The outer side rotation shaft (111) is supported by the motor housing (108) through a bearing (117) so as to rotate. The inner side rotation shaft (112) is supported by the outer side rotation shaft (111) through a bearing (118) so as to relatively rotate. Accordingly, the outer side rotation shaft (111) and the inner side rotation shaft (112) are configured to rotate independently.

A male screw portion (111a) is provided in a right end portion of the outer side rotating shaft (111), and a first female screw member (119) is screwed to the male screw portion (111a). A right end portion of the inner side rotation shaft (112) protrudes to the right direction from a right end of the outer side rotating shaft (111), and a male screw portion (112a) is provided in the right end portion and a second female member (120) is screwed to the male screw portion (112a).

Respective female screw members (119) (120) are slidably fitted to a pair of guide bars (121) which are fixed to the frame (107) and extend to the right direction in parallel to the respective rotating shafts (111) (112). Accordingly, the respective female screw members (119) (120) are not able to rotate, and move in the right and left direction (axial direction of the respective rotating shafts (111) (112)) with the rotation of the respective rotating shafts (111) (112).

A first coupling member (122) engaged with the sleeve (102) and coupling the first female screw member (119) and the sleeve (102) is fixed to the first female screw member (119) screwed to the outer side rotating shaft (111). Accordingly, the first female screw member (119) and the sleeve (102) integrally move in the axial direction with the rotation of the outer side rotating shaft (111).

A second coupling member (123) engaged with the spline cylinder (104) and coupling the second female member (120) and the spline cylinder (104) is fixed to the second female screw member (120) screwed to the inner side rotating shaft (112). Accordingly, the second female screw member (120) and the spline cylinder (104) integrally move in the axial direction with the rotation of the inner side rotating shaft (112).

An axial direction drive means (98) moving the sleeve (102) as an axial direction moving means includes the first motor (109), the outer side rotation shaft (111), the first female screw member (119) and the first coupling member (122).

A circumferential direction drive means (99) moving the spline cylinder (104) as a circumferential direction moving member includes the second motor (110), the inner side rotating shaft (112), the second female screw member (120) and the second coupling member (123).

The controller (124) controlling the first motor (109) adjusts an axial direction position of the plate cylinder (47) by driving the first motor (109) in accordance with a printing misalignment value of a can (C) in a height direction in the printing misalignment value measurement means (56) of the can inspection device (5). The controller (125) controlling the second motor (110) adjusts a circumferential direction position of the plate cylinder by driving the second motor (110) in accordance with a printing misalignment value of a can (C) in a circumferential direction in the printing misalignment value measurement means (56).

Specific structures of mechanical portions of the can inspection device (5) according to the embodiment of the present invention are shown in FIG. 9 to FIG. 12.

The can inspection device (5) includes a loading conveyor (61) sequentially loading cans (C) for inspection, a take-out device (62) provided at an end part of the loading conveyor (61) and taking out the cans (C) for inspection from the loading conveyer (61), the can rotation device (51) holding the cans (C) for inspection taken out in the take-out device (62) and rotating the cans (C), the imaging device (52) taking images of the cans (C), a controller (not shown) formed of a computer having a CPU executing logical operation of the image processor (53), a ROM storing control programs, a RAM storing data and so on, a display displaying image processing results and so on, an unloading conveyor (63) unloading cans (C) as good products and a discharge chute (64) discharging cans (C') as inspection rejected products.

The take-out device (62) includes a suction part (65) adsorbing cans fed by the loading conveyor (61) and pushed out and a cylinder part (66) moving the suction part (65) upward. The suction part (65) has a semi-cylindrical concave portion (65a) to which an intermediate portion of the can (C) is fitted.

The can rotation device (51) includes a main shaft (71) rotated by a motor (72) and a rotating disk (73) attached to the main shaft (71). The motor (72) is attached to an upper surface of a top wall of a housing (70), and the main shaft (71) is rotatably supported at the top wall of the housing (70).

The rotating disk (73) is concentric with the main shaft (71), rotating integrally with the main shaft (71). In an outer periphery of the rotating disk (73), plural arms (73a) are provided so as to protrude outward in a radial direction at equal intervals. Vertical driven side rotating shafts (74) are supported in respective arms (73a) of the rotating disk (73) so as to rotate freely. Holding members (75) formed concentrically with the driven side rotating shafts (74) so as to hold the cans (C) are attached to the driven side rotating shafts (74).

The driven side rotating shafts (74) revolve around the main shaft (71) through the set position of the take-out device (62), the set position of the imaging device (52), the set position of the unloading conveyor (63) and the set position of the discharge chute (64) with the rotation of the rotating disk (73) so as to return to the set position of the take-out device (62).

A driving device (76) for rotating (revolving) the driven side rotating shaft (74) is arranged above the driven side rotating shaft (74) positioned in the set position of the imaging device (52) so as to be supported on the top wall of the housing (70). The driving device (76) includes a vertical drive side rotating shaft (77) and a motor (78) provided in concentric with the drive side rotating shaft (77).

As the imaging device (52), a first camera (79) taking an image of the entire can and a second camera (80) taking an image of an opening-side end portion of the can are used. The image taken by the first camera (79) is used in the image inspection means (54) and the density measurement means (55). The image taken by the second camera (80) is used in the printing misalignment value measurement means (56).

In the set position of the imaging device (52), the drive side rotating shaft (77) faces the driven side rotating shaft (74) in the axial direction, and magnets (81) (82) applying attracting forces to each other are fixed to a lower end portion of the drive side rotating shaft (77) and an upper end portion of the driven side rotating shaft (74). Accordingly, a lower surface of the magnet (81) provided in the lower end of the drive side rotating shaft (77) and an upper surface of the magnet (82) provided on an upper end of the drive side rotating shaft (74) are adsorbed (integrated) by respective attracting forces of the magnets (81) (82).

The driven side rotating shafts (74) are supported by cylindrical casings (83) provided in respective arms (73a) of the rotating disk (73) so as to rotate and so as not to move in the axial direction.

Figure 12:
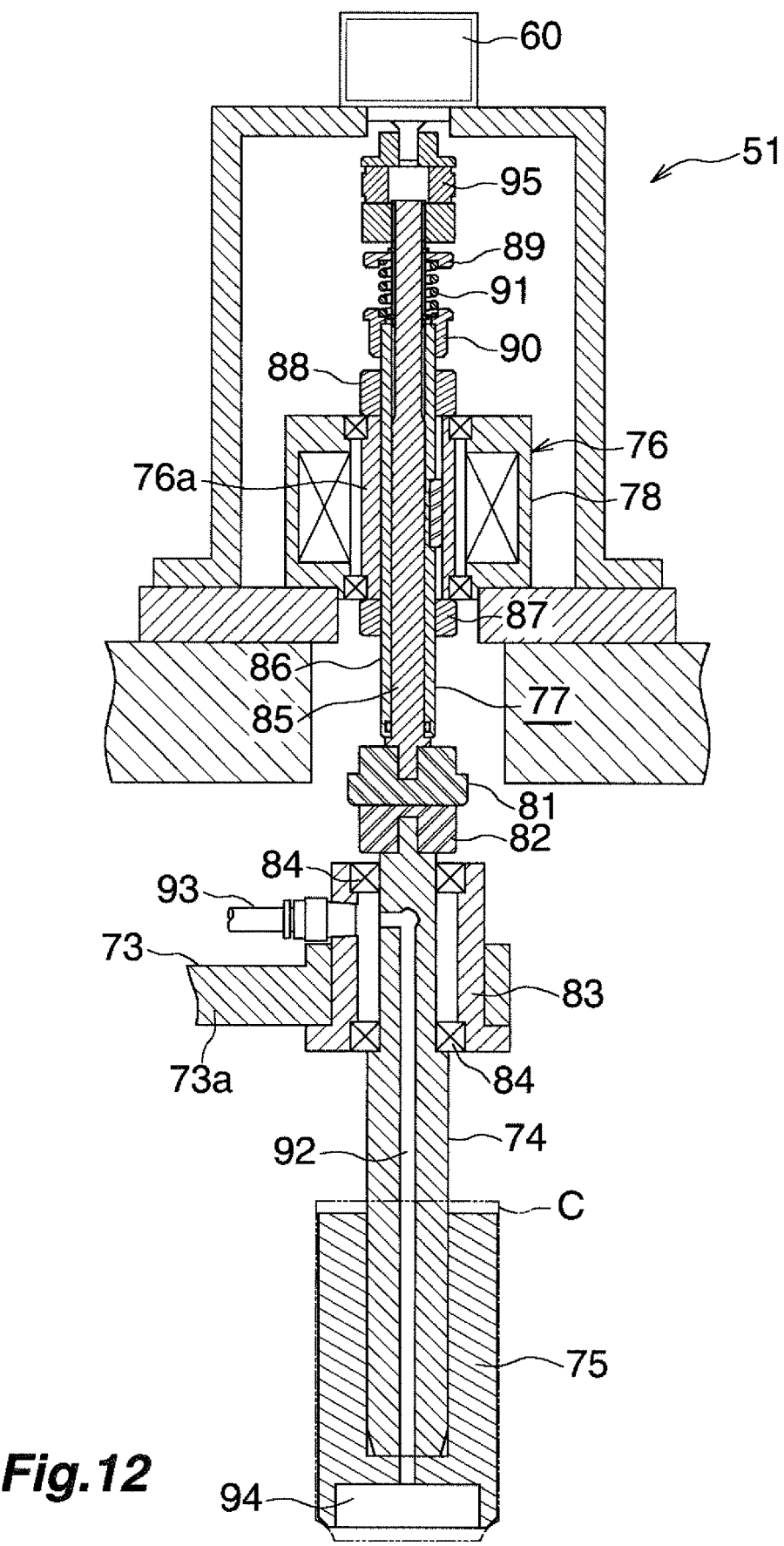
FIG. 12 is a vertical cross-sectional view showing a rotation device of the can inspection device.

As shown in FIG. 12, the drive side rotating shaft (77) includes a solid shaft portion (85) and an outer cylindrical portion (86) spline-fitted to the shaft portion (85) concentrically with the shaft portion (85). A lower end portion of the shaft portion (85) slightly protrudes downward from a lower end of the outer cylindrical portion (86) and the magnet (81) is attached to the lower end portion of the shaft portion (85). An upper part of the shaft portion (85) protrudes upward as compared with an upper end of the outer cylindrical portion (86), and a rotary encoder (60) detecting a rotation speed (rotation angle) of the drive side rotating shaft (77) is attached to an upper end of the shaft portion (85) through a coupling (95).

A male screw is formed on an outer periphery of the outer cylindrical portion (86), and a screw (87) screwed to a lower portion of the outer cylindrical portion (86) and a screw (88) screwed to an upper portion of the outer cylindrical portion (86) sandwich a motor rotor (76a) arranged on an outer periphery of the outer cylindrical portion (86) from upper and lower sides, therefore, the outer cylindrical portion (86) rotates integrally with the motor rotor (76a). The shaft portion (85) spline-fitted to the outer cylindrical portion (86) integrally rotates accordingly. The shaft portion (85) can relatively move in the axial direction with respect to the outer cylindrical portion (86).

The driven side rotating shaft (74) is supported by the casing (83) through a bearing (84). The drive side rotating shaft (77) and the driven side rotating shaft (74) are coupled (adsorbed) by the attracting forces of the magnets (81) (82), and the driven side rotating shaft (74) rotates integrally with the rotation of the driven side rotating shaft (74).

Annular spring brackets (89) (90) are fixed to an upper end portion of the shaft portion (85) of the drive side rotating shaft (77) and an upper end portion of the outer cylindrical portion (86), and a compressed coil spring (91) is arranged between both spring brackets (89) (90). Therefore, when the shaft portion (85) moves downward, the compressed coil spring (91) is further compressed and biases the shaft portion (85) upward, which prevents the shaft portion (85) from moving downward. Accordingly, the magnets (81) (82) applying attracting forces to each other do not contact each other, which prevents abrasion between the magnets (81) (82).

The drive side rotating shaft (77) rotates by being driven by the motor (78), and the can (C) held by the driven side rotating shaft (74) rotates with the rotation, and an image of one rotation is captured by imaging device (52). At this time, a period for one pixel is determined so as to correspond to an output of the rotary encoder (60) for eliminating an error.

The rotation of the can (C) and the rotation of the rotary encoder (60) (rotation of the drive side rotating shaft (77)) are rotated so as to be synchronized with each other for eliminating the error. According to this, an output (pulse) of the rotary encoder (60) and the flow of the image for one pixel are synchronized. Even when an uneven rotation occurs in respective cans (C) to be measured, taken images of respective cans are not extended/contracted and stable inspections are performed.

An air vent passage (92) one end of which opens to a lower end and the other of which opens to an outer periphery in the vicinity of an upper end portion is provided in the driven side rotation shaft (74). A pipe for evacuation (93) for evacuating the air vent passage (92) is attached to the casing (83).

The holding member (75) is made of resin and has a cylindrical shape, and a cylindrical suction chamber (94) opening downward is provided in a lower end portion of the holding member (75). The air vent passage (92) of the driven side rotation shaft (74) is communicated to the suction chamber (94). The suction chamber (94) becomes in a negative pressure (vacuum) by evacuating the suction chamber (94) by a not shown vacuum pump through the pipe for evacuation (93), and the can (C) is held by the holding member (75).

In the imaging device (5), an image of the print surface of the can (C) is started to be taken from an arbitrary position of the can (C) in a state where the can (C) rotates at an arbitrary speed.

In printing for one turn, when a print end position abuts on a print start position, printing of one turn is just performed. As the printing is slightly misaligned in respective cans at the abutting part between the print end position and the print start position, a large misalignment occurs when the abutting part exists at an intermediate part in image capturing. Therefore, when a range from a designation mark to a designation mark is defined as one turn, the abutting part of printing is included in the intermediate part, which is not desirable. Accordingly, an image for one turn from the print start position to the print end position is captured at the time of capturing the image. As the designation marks, marks which can be easily found in printed images are used, for example, bar codes are used.

Figure 13:
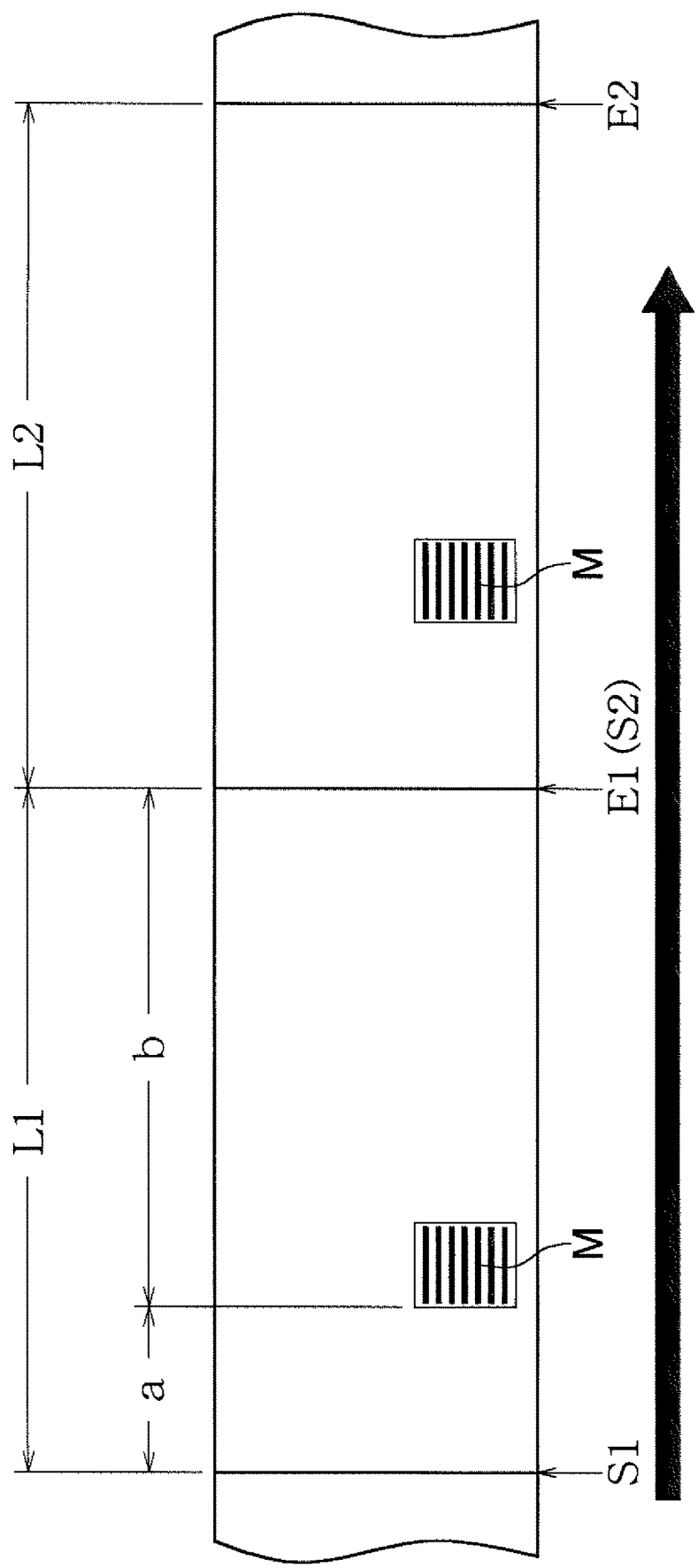
FIG. 13 is a view schematically showing a step of capturing images by the can inspection device.

As the position of the can (C) fed to the inspection device (5) is not specified, positions of the can (C) facing the cameras (79) (80) are at random. Therefore, it is necessary to find the print start position for capturing the image for one turn. Accordingly, in an operation of capturing the image, as distances (angles) from a designation mark (M) to print start positions (S1) (S2) are previously known in FIG. 13, first, the designation mark (M) should be found, and after the designation mark (M) is found, a position obtained by moving in a reverse direction by "a" as a distance corresponding to the angle is determined as the print start position (S1), namely, the image capturing start position. It is also possible to determine a position obtained by moving in a positive direction by "b" as the print start position (S2), namely, the image capturing start position. Accordingly, it is possible to capture an image of just one turn from the print start position (S1)/(S2) to the print end position (E1)/(E2) which is shown by "L1" or "L2".

The image inspection by the image inspection means (54) of the inspection device (5) has been hitherto performed, in which a master image and a taken image are compared pixel by pixel by the image inspection means (54) to thereby perform inspections for a partial lack, a stain due to ink scattering and so on in the image. In the image inspection means (54), a product having a lack with a size exceeding a predetermined size is determined as an inspection rejected product, and a product exceeding a misalignment allowable value with respect to the master image is also determined as an inspection rejected product.

Figure 14:
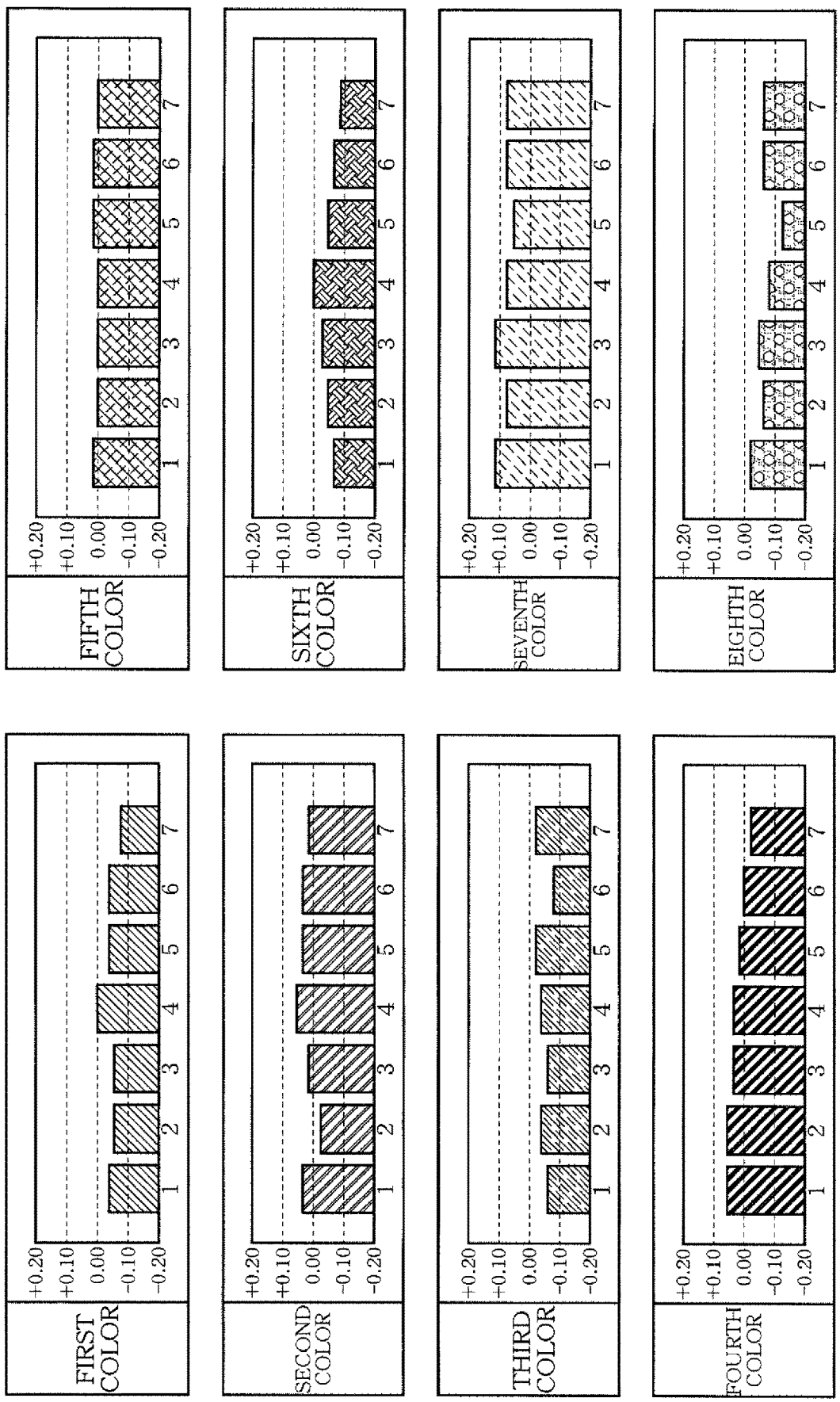
FIG. 14 is a view showing density data obtained from the can inspection device.

The inspection by the density measurement means (55) of the inspection device (5) is performed with respect to single-color solid portions. That is, as it is difficult to measure the density at a place where plural colors overlap, therefore, places where the single-color solid portions exist are designated in advance for respective colors, and densities in the designated places (density measuring places) are measured. A density value may be calculated as an arithmetic mean value of RGB components of pixels defined as the density measurement place, and can be obtained as a density difference between the density at each place and the density of the master image. In the case where the single-color solid portion has, for example, a size of 0.8 mm×0.8 mm, the density can be measured. When it is difficult to measure the density accurately because the size is not able to be secured or other reasons, whether the density difference with respect to the master image is within a reference or not is just determined. Densities corresponding to the number (seven) of ink transfer rollers (15) can be obtained for one color as shown in FIG. 14. As the number of colors (the number of plate cylinders) is eight in the embodiment, density measurement values of 8×7 can be obtained. The density measurement results shown in FIG. 14 are displayed on the display of the inspection device (5).

The density measurement results are fed back to the printer (2) by the inspection result feedback controller (49) without human intervention, and thus, positions of respective ink transfer rollers (15) are controlled by the controller (34) of the ink supply devices (3) to change the amount of ink to be supplied. Accordingly, a good print state can be maintained in the printer (2) by correcting densities before a defective product in density is found.

The image inspection means (54) and the density measurement means (55) are executed by using the image of the entire can taken by the first camera (79), however, the printing misalignment value measurement means (56) are executed by using the image taken by the second camera (80) taking an image of an opening-side end portion of the can.

Figure 15A:
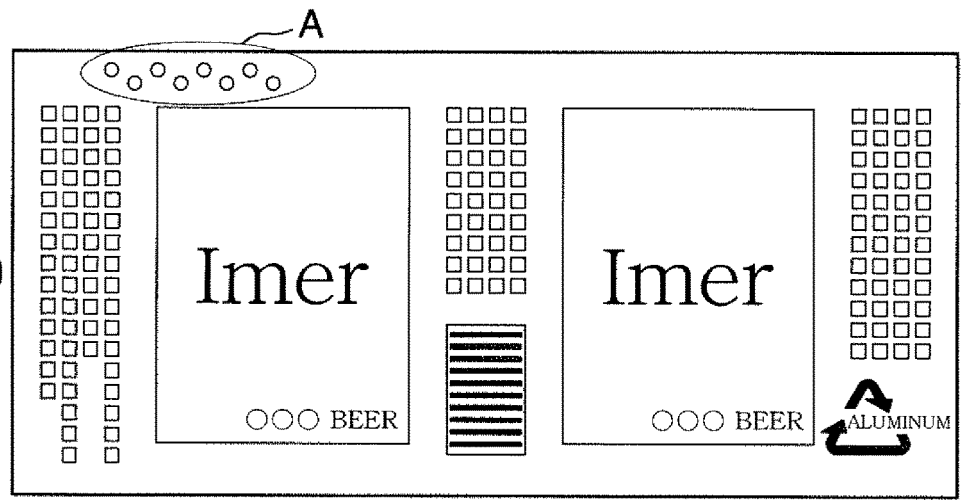
FIGS. 15(a), (b), and (c) are views showing printing misalignment data obtained from the can inspection device.

The opening-side end portion of the can (C) is a portion covered with a lid, which is a portion where printing has not been performed and where inspection has not been required in related-art cans. Concerning cans (C) to be inspected by the inspection device (5) according to the embodiment, printing misalignment value inspection marks are printed for respective colors on the opening-side end portion of the can (C). That is, as shown in FIG. 15(a), the printing misalignment value inspection marks shown by "A" are added on the print surface of the can (C) in addition to previously existing items such as a product name, a company name, ingredients and a bar code.

Figure 15B:
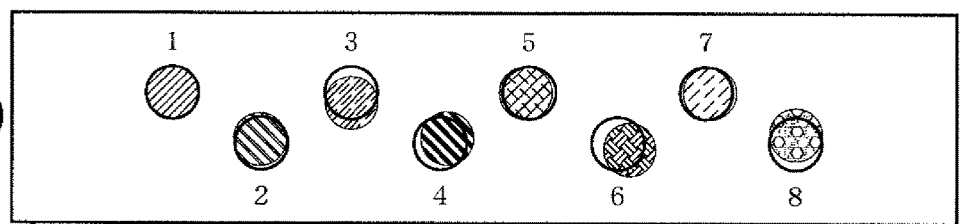
Figure 15C:
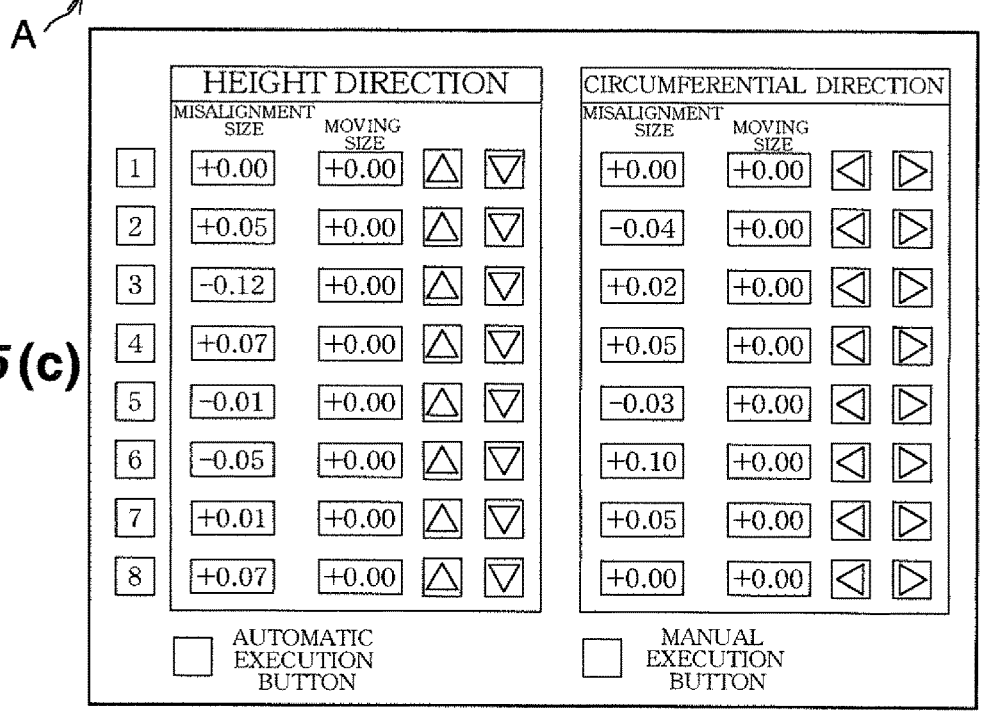

The printing misalignment value inspection marks (A) are provided for the total eight colors from one to eight as shown in FIG. 15(b) in an enlarged manner. Positions shown by solid lines in the drawing are reference positions (positions of designation marks in the master image), and positions shown by two-dot chain lines in the drawing are positions of respective colors obtained from the taken image. According to the drawing, it is found that, for example, printing misalignment is extremely small in a color of No. 7, a printing misalignment value in the height direction of the can (C) is large in a color of No. 3, and a printing misalignment value in a circumferential direction of the can (C) is large in a color of No. 6. The printing misalignment value is calculated as a value indicating to what degree (or how long (mm)) (as the number of pixels) the position of the designation mark in the master image is deviated from the position of the designation mark in the taken image, and calculated numerals are displayed on the display of the inspection device (5) as shown in FIG. 15(c). The misalignment amounts are calculated in the height direction of the can (axial direction of the plate cylinder (47)) and in the circumferential direction of the can (circumferential direction of the plate cylinder (47)) respectively. The printing misalignment measurement results are fed back to the printer (2) by the inspection result feedback controller (49) without human intervention. The printing misalignment measurement results may also be fed back to the printer (2) not by using the inspection result feedback controller (49) (may be also fed back manually).

The controller (34) of the ink supply device (3) controls the contact period in the ink supply device (3) based on a density target value which is previously set, and the density measurement results obtained in the density measurement means (55) of the can inspection device (5) are added to the control. Specifically, when the density of a certain color is lower than a target value at a certain place, a contact length between the ink transfer roller supplying the color to the place and the inkwell roller is elongated, thereby increasing the density. When the density of a certain color is higher than a target value at a certain place, the contact length between the ink transfer roller supplying the color to the place and the inkwell roller is shortened.

In the example shown in FIG. 14, for example, the density is relatively high at a place of No. 4 and is relatively low at a place of No. 7 in the first color. In the second color, the density is relatively high at a place of No. 4 and the density is relatively low at a place of No. 2. When such density measurement results are outputted to the printer (2), in the controller (34) of the ink supply device (3) of the printer (2), for example, the contact length between the ink transfer roller of No. 4 which supplies the ink to the plate cylinder of the first color and the inkwell roller is shortened, and the contact length between the ink transfer roller of No. 7 which supplies the ink to the plate cylinder of the first color and the inkwell roller is lengthened based on the input of the density measurement results. Accordingly, the density of the first color is changed to be uniform as the whole. The same process is performed to other colors.

The density measurement results in the can inspection device (5) are fed back to the printer (2) immediately as described above, and the positions of respective ink transfer rollers (15) are controlled by the controller (34) of the ink supply devices (3) to thereby change the amount of ink to be supplied. Accordingly, the density can be corrected before a defective product in density is found, which can prevent generation of the defective product in density.

The printing misalignment value of the can (C) in the height direction is fed to the controller (124) which controls the first motor (109) of the registration device (58), and the controller (124) drives the first motor (109) in accordance with the printing misalignment value, thereby automatically adjusting the position of the plate cylinder (47) in the axial direction. The printing misalignment value of the can (C) in the circumferential direction is fed to the controller (125) which controls the second motor (110) of the registration device (58), and the controller (125) drives the second motor (110) in accordance with the printing misalignment value, thereby automatically adjusting the position of the plate cylinder (47) in the circumferential direction.

The printing misalignment value measurement results in the can inspection device (5) are immediately fed back to the printer (2) by the inspection result feedback controller (49), and the positional adjustment (registration) of the plate cylinder (47) is performed by the registration device (58). Accordingly, the printing misalignment value can be corrected before a defective product in printing misalignment is found, which can prevent generation of the defective product in printing misalignment.

INDUSTRIAL APPLICABILITY

When adopting the can printing apparatus according to the present invention, printing conditions of the printer are changed based on inspection results of the can inspection device, therefore, printing defects are solved in an early stage, as a result, it is possible to contribute to the improvement of printing accuracy and labor saving in the printer.

The invention claimed is:

1. A can inspection device comprising:
   an imaging device taking images of rotating cans; and
   an image processor processing taken images,
   which is provided in a can printing apparatus, performing inspections of print states of the cans and feeding back inspection results to the can printing apparatus,
   wherein the imaging device includes a first camera facing to an entire can from a direction orthogonal to an axial direction of the can and taking an image of the entire can and a second camera facing to an opening-side end portion of the can from a direction orthogonal to the axial direction of the can and taking an image of the opening-side end portion of the can, wherein
   whether printing is performed properly as compared with a master image is inspected, densities in designated positions for respective colors are measured by using the image taken by the first camera, and misalignment values with respect to set positions of printing misalignment inspection marks printed on the opening-side end portion of the can for respective colors are measured by using the image taken by the second camera,
   wherein the image processor is configured to:
      inspect whether the printing is performed properly as compared with the master image,
      measure densities in the designated positions for respective colors by using the image taken by the first camera, and
      measure the misalignment values with respect to the set positions of the printing misalignment inspection marks printed for respective colors by using the image taken by the second camera.

2. The can inspection device according to claim 1,
   wherein a rotation device for rotating cans includes a vertical drive side rotating shaft driven by a motor, a vertical driven side rotating shaft rotating integrally with the drive side rotating shaft, a cylindrical holding member attached concentrically to the driven side rotating shaft so as to hold a can and an encoder detecting a rotation of the drive side rotating shaft, and
   the drive side rotating shaft and the driven side rotating shaft face each other in the axial direction in a state of being positioned in a vertical direction, and magnets applying attracting forces to each other are provided to a lower end portion of the drive side rotating shaft and an upper end portion of the driven side rotating shaft, thereby allowing the drive side rotating shaft and the driven side rotating shaft to rotate integrally.

3. A can inspection system comprising:
cans having printing misalignment inspection marks on an opening-side end portion thereof; and
the can inspection device according to claim 1.

4. A can inspection device comprising:
a rotation device rotating cans;
an imaging device taking images of rotating cans; and
an image processor processing taken images,
which is provided in a can printing apparatus, performing inspections of print states of the cans and feeding back inspection results to the can printing apparatus,
wherein the imaging device includes a first camera taking an image of the entire can and a second camera taking an image of an opening-side end portion of the can, wherein
whether printing is performed properly as compared with a master image is inspected, densities in designated positions for respective colors are measured by using the image taken by the first camera,
and misalignment values with respect to set positions of printing misalignment inspection marks printed on the opening-side end portion of the can for respective colors are measured by using the image taken by the second camera,
wherein the rotation device includes a vertical drive side rotating shaft driven by a motor, a vertical driven side rotating shaft rotating integrally with the drive side rotating shaft, a cylindrical holding member attached concentrically to the driven side rotating shaft so as to hold a can and an encoder detecting a rotation of the drive side rotating shaft.

5. A can inspection device comprising:
an imaging device taking images of rotating cans;
an image processor processing taken images; and
a conveyance device conveying cans,
which is provided in a can printing apparatus, performing inspections of print states of the cans and feeding back inspection results to the can printing apparatus,
wherein the imaging device includes a first camera facing to an entire can from a direction orthogonal to an axial direction of the can and taking an image of the entire can and a second camera facing to an opening-side end portion of the can from a direction orthogonal to the axial direction of the can and taking an image of the opening-side end portion of the can,
wherein whether printing is performed properly as compared with a master image is inspected, densities in designated positions for respective colors are measured by using the image taken by the first camera, and misalignment values with respect to set positions of printing misalignment inspection marks printed on the opening-side end portion of the can for respective colors are measured by using the image taken by the second camera, and
wherein the conveyance device comprises:
  a sampling line transferring part of a number of cans printed by the can printing apparatus to the imaging device; and
  a return line returning the cans determined as good products in the can inspection device to a conveyance line of the can printing apparatus.

6. The can inspection device according to claim 5,
wherein the can is rotated by a rotation device, and a drive side of the rotation device and the can on the driven side are synchronized through an encoder.

* * * * *